(12) United States Patent
Gallie

(10) Patent No.: US 6,903,246 B2
(45) Date of Patent: Jun. 7, 2005

(54) **DEHYDROASCORBATE REDUCTASE ("DHAR") GENES FROM *TRITICUM AESTIVUM* AND THEIR USE TO MODULATE ASCORBIC ACID LEVELS IN PLANTS**

(75) Inventor: Daniel R. Gallie, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 222 days.

(21) Appl. No.: 10/161,195

(22) Filed: May 28, 2002

(65) Prior Publication Data

US 2003/0215949 A1 Nov. 20, 2003

(51) Int. Cl.[7] ............................. A01H 1/00; A01H 5/00; C12N 15/82; C12N 15/52
(52) U.S. Cl. ...................... 800/298; 800/278; 800/294; 800/293; 800/287; 536/23.2
(58) Field of Search ................................. 800/278, 294, 800/293, 298, 287; 536/23.2, 23.6; 435/320.1, 419

(56) References Cited

U.S. PATENT DOCUMENTS 6,518,486 B1 * 2/2003 McKersie et al. .......... 800/298

OTHER PUBLICATIONS

Tang et al, 1999, Plant Cell 11:177–189.*
Colliver et al, 1997, Plant Mol. Biol. 35:509–522.*
D'Ascenzo et al, 1999, GenBank Accession No. AW093721.*
Klann et al, 1996, Plant Physiol. 112:1321–1330.*
Mckerseie et al, Provisional U.S. Appl. No. 60/089,197, filed Jun. 1998.*
Chen and Gallie, Plant Cell 16:1143–1162 (2004).*
Chen et al, Proc Natl Acad Sci USA. 100:3525–30 (2003).*
Conklin, P.L. et al. "Environmental stress sensitivity of an ascorbic acid–deficient Arabidopsis mutant," *PNAS USA* Sep. 1996, pp. 9970–9974, vol. 93.
Conklin, P.L. et al. "Identification of ascorbic acid–deficient *Arabidopsis thaliana* mutants," *Genetics* Feb. 2000, pp. 847–856, vol. 154.
Horemans, N. et al. "The ascorbate carrier of higher plant plasma membranes preferentially translocates the fully oxidized (dehydroascorbate) molecule," *Plant Physiol.* l1997, pp. 1247–1253, vol. 114.
Horemans, N. et al. "Transport and action of ascorbate at the plant plasma membrane," *Trends in Plant Sci.* (reviews) Jun. 2000, pp. 1360–267, vol. 5, No. 6.
Leung, J. and Giraudat, J. "Abscisic acid signal transduction," *Annu. Rev. Plant Physiol. Plant Mol. Biol.* 1998, pp. 199–222, vol. 49.

McAinsh, M.R. et al. "Changes in stomatal behavior and guard cell cytosolic free calcium in response to oxidative stress," *Plant Physiol.* 1996, pp. 1031–1042, vol. 111.
Morrell, S. et al. "Dehydroascorbate and dehydroascorbate reductase are phantom indicators of oxidative stress in plants," *FEBS Lett.* 1997, pp. 567–570, vol. 414.
Morrell, S. et al. "Dehydroascorbate reduction: the phantom remaining," *FEBS Lett.* 1998, pp. 530–531, vol. 425.
Noctor, G. and Foyer, C.H. "Ascorbate and glutathione: keeping active oxygen under control," *Annu. Rev. Plant Physiol. Plant Mol. Biol.* 1998, pp. 249–279, vol. 49.
Pallanca, J. and Smirnoff, N. "The control of ascorbic acid synthesis and turnover in pea seedlings," *J. of Experimental Botany* Apr. 2000, pp. 669–674, vol. 51, No. 345.
Pei, Z. et al. "Calcium channels activated by hydrogen peroxide mediate abscisic acid signaling in guard cells," *Nature* Aug. 17, 2000, pp. 731–734, vol. 406.
Rautenkranz, A.A.F. et al. "Transport of ascorbic and dehydroascorbic acids across protoplast and vacuole membranes isolated from barley (*hordeum vulgare* l. cv gerbel) leaves," *Plant Physiol.* 1994, pp. 187–193, vol. 106.
Shimaoka, T. et al. "Purification and characterization of chloroplast dehydroascorbate reductase from spinach leaves," *Plant Cell Physiol.* 2000, pp. 1110–1118, vol. 41, No. 10.
Siendones, E. et al. "Biosynthesis of ascorbic acid in kidney bean. L–galactono–Γ–lactone dehydrogenase is an intrinsic protein located at the mitochondrial inner membrane," *Plant Physiol.* Jul. 1999, pp. 907–912, vol. 120.
Smirnoff, N. "Ascorbate biosynthesis and function in photoprotection," *Phil. Trans. R. Soc. Lond.* 2000, pp. 1455–1465, vol. 355.
Urano, J. et al. "Molecular cloning and characterization of a rice dehydroascorbate reductase," *FEBS Lett.* 2000, pp. 107–111, vol. 466.
Van Breusegem et al. "Effects of overproduction of tobacco MnSOD in maize chloroplasts on foliar tolerance to cold and oxidative stress," *J. of Exper. Botany* Jan. 1999, pp. 71–78, vol. 50, No. 330.
Xiang, C. et al. "The biological functions of glutathione revisited in arabidopsis transgenic plants with altered glutathione levels," *Plant Physiol.* Jun. 2001, pp. 564–574, vol. 126.
Zhang, X. et al. "Hydrogen peroxide is involved in abscisic acid–induced stomatal closure in *Vicia faba*," *Plant Physiol.* Aug. 2001, pp. 1438–1448, vol. 126.

* cited by examiner

*Primary Examiner*—Anne Kubelik
(74) *Attorney, Agent, or Firm*—Townsend & Townsend & Crew

(57) ABSTRACT

The invention is directed to a new dehydroascorbate reductase ("DHAR") genes from Triticum aestivum, which is useful in modulating ascorbic acid levels in plants.

29 Claims, No Drawings

DEHYDROASCORBATE REDUCTASE ("DHAR") GENES FROM *TRITICUM AESTIVUM* AND THEIR USE TO MODULATE ASCORBIC ACID LEVELS IN PLANTS

STATEMENT AS TO RIGHTS TO INVENTIONS MADE UNDER FEDERALLY SPONSORED RESEARCH OR DEVELOPMENT

This invention was made with Government support under Grant Number 9835100-6150 awarded by the United States Department of Agriculture. The Government has certain rights in this invention.

FIELD OF THE INVENTION

The present invention is generally related to plant genetic engineering. In particular, the invention is directed to new dehydroascorbate reductase ("DHAR") genes useful in modulating ascorbic acid levels in plants.

BACKGROUND OF THE INVENTION

Despite its essential role in supporting life, oxygen can be highly damaging to an organism under certain conditions. For plants, the inadvertent production of active oxygen species (e.g., $O_2^-$, $H_2O_2$, hydroxyl radicals, and singlet oxygen) occurs as a consequence of normal photosynthetic activity. Exposure to many abiotic stresses can exacerbate the production of active oxygen species, including cold, drought, salt, or high light. The production of active oxygen species near the photosynthetic machinery can result in substantial damage and thus reduce photosynthetic capacity or, under severe conditions, lead to death of the organ or entire plant. Active oxygen species can be produced in other cellular compartments including the mitochondria which themselves have substantial electron transport activity as well as in peroxisomes during the oxidation of glycollate. Active oxygen species are produced in response to attack by many pathogens. Nevertheless, not all active oxygen species are produced by plant processes or responses. Active oxygen species can invade a plant when it is exposed to pollutants such as ozone. However, the production of active oxygen species is not always inadvertent. Active oxygen species can play an important role as signaling molecules. For example, oxygen photoreduction (the Mehler peroxidase reaction) results from the transfer of electrons from photosystem I (PSI) to oxygen to form superoxides which disproportionates to hydrogen peroxide ($H_2O_2$), a reaction that is catalyzed by superoxide dismutase. The Mehler reaction thus serves to maintain electron flow through PSI and maintains its correct function. $H_2O_2$ acts as a signaling molecule involved in many stress and defense responses (Van Breusegem et al., 2001) and in guard cells can induce stomatal closure (Pei et al., 2000; Zhang et al., 2001). Consequently, plants have had to evolve mechanisms to limit the deleterious effects of many active oxygen species and simultaneously use the production or exposure of certain active oxygen species as information about alterations to the internal or external environment of the plant to mount correct responses to its current conditions. Plants, like most organisms, rely on an array of antioxidants to detoxify active oxygen species.

Of the antioxidants found in plants, ascorbic acid ("ASC") is the most abundant and is present in millimolar concentrations that range from 10 to 300 mM (Smirnoff, 2000). Glutathione, for example, the other major soluble antioxidant, is typically present at only 10% of the concentration of ASC (Noctor and Foyer, 1998). In its antioxidant role, ASC is used by ascorbate peroxidase to convert $H_2O_2$ to water and ASC can directly scavenge superoxide, hydroxyl radicals, and singlet oxygen. ASC also contributes to the regulation of the cellular redox state and is used to regenerate a-tocopherol from a-tocopherol radicals that are produced from the reduction of lipid peroxyl radicals. ASC can serve as an enzyme co-factor, e.g., for violaxanthin de-epoxidase (VDE) (Eskling et al., 1997) which catalyzes the conversion of violaxanthin to zeaxanthin (the Xanthophyll cycle), which is required for the dissipation of excess excitation energy during non-photochemical quenching. ASC is also involved in the regulation of cell elongation and progression through the cell cycle (reviewed in Horemans et al., 2000). This partial list of cellular functions demonstrates the importance of ASC to the health and growth of the cell, and ultimately, the plant.

ASC biosynthesis differs from that in mammals and has been shown to result from the oxidation of L-galactose to L-galactono-1,4-lactone which in turn is oxidized to ASC by L-galactono-1,4-lactone dehydrogenase. Although most of the biosynthetic pathway is carried out in the cytosol, the final step occurs at the inner mitochondrial membrane where the L-galactono-1,4-lactone dehydrogenase is located (Siendones et al., 1999; Bartoli et al., 2000). Feedback inhibition of ASC synthesis by the ASC pool size has been demonstrated (Pallanca and Smirnoff, 2000). Given that ASC is present in most compartments of the cell including the mitochondria, cytosol, chloroplast stroma and thylakoid lumen, and apoplast, it is transported throughout the cell and to the apoplast through specific transport across the chloroplast envelope and plasma membrane (Rautenkranz et al., 1994; Horemans et al., 1997). Following its use by ascorbate peroxidase in $H_2O_2$ detoxification, its participation in the Xanthophyll cycle, or its reduction of a-tocopherol radicals as part of non-photochemical quenching, ASC is oxidized to the monodehydroascorbate (MDHA) radical which disproportionates to ASC and dehydroascorbate (DHA). Although the rate of ASC synthesis is not fast, ASC is rapidly regenerated from DHA, a reaction catalyzed by DHAR and which uses glutathione as the reductant. Glutathione reductase uses NADPH produced principally from PSI to regenerate glutathione from oxidized glutathione. Consequently, the detoxification of AOS species by this ascorbate-glutathione pathway involves the transfer of electrons from PSI to NADPH to glutathione to ASC to $H_2O_2$ in a series of reactions in which there is no net loss of ASC or glutathione. Given its role in regenerating ASC, the principal function of DHAR activity would be expected to maintain the existing pool of ASC in a reduced state needed to meet the challenge imposed by those stresses that generate active oxygen species.

As an antioxidant, one of ASC's role in plants is to scavenge hydrogen peroxide. Hydrogen peroxide is involved in regulating the stomatal openings formed by the presence of pairs of guard cells in plants. Stomatal closure can be triggered by an increase in the intracellular concentration of hydrogen peroxide in guard cells. Stomatal openings can be triggered by a decrease in the intracellular concentration of hydrogen peroxide in guard cells. Plants control exposure to environmental conditions by tightly regulating stomatal aperture. Stomatal closures limits exposure to plants of certain toxins that may be circulating in the environment and protect the plant from drought conditions. Stomatal closures, however, also limit $CO_2$ assimilation and increase the concentration of NADPH in plants as a consequence of reduction in Calvin cycle activity. Because of the importance of ASC levels in plants, there exists a need for closely regulating its production. This invention meets this and other needs.

SUMMARY OF THE INVENTION

The present invention provides DHAR nucleic acids and polypeptides. In one aspect of the present invention, the invention provides an isolated nucleic acid encoding a DHAR polypeptide comprising an amino acid sequence at least 80% identical to SEQ ID NO: 1, wherein the sequence is not SEQ ID NO: 9, SEQ ID NO: 13 or SEQ ID NO: 15.

In a second aspect of the present invention, a DHAR nucleic acid of the present invention further comprises a chloroplast transit signal sequence.

In a third aspect of the present invention, a DHAR nucleic acid is isolated from wheat, tobacco, maize, or tomato.

In a fourth aspect, the present invention provides a recombinant expression cassette comprising a promoter sequence operably linked to a nucleic acid encoding a DHAR polypeptide comprising an amino acid sequence at least 80% identical to SEQ ID NO: 1. In one embodiment of the present invention, the nucleic acid is operably linked to the promoter sequence in an antisense orientation. In a second embodiment, the nucleic acid is isolated from wheat, tobacco, maize, tomato, rice, or spinach. In a third embodiment, the promoter is a constitutive promoter. In a fourth embodiment, the promoter is an organ specific promoter. In a fifth embodiment, the promoter preferentially directs expression in guard cells. In a sixth embodiment, the nucleic acid encodes a DHAR polypeptide comprising an amino acid sequence substantially identical to SEQ ID NOs: 3, 5, 7, 9, 11, 13, or 15. In a seventh embodiment, the nucleic acid encodes a DHAR polypeptide comprising an amino acid sequence comprising SEQ ID NOs. 3, 5, 7, 9, 11, 13, or 15.

In a fifth aspect, the present invention provides a transgenic plant comprising a recombinant expression cassette comprising a plant promoter sequence operably linked to a nucleic acid encoding a DHAR polypeptide comprising an amino acid sequence at least 80% identical to SEQ ID NO: 1. In one embodiment, the plant is wheat, tobacco, maize, tomato, spinach, or rice. In a second embodiment, the nucleic acid is operably linked to the promoter sequence in an antisense orientation. In a third embodiment, the promoter is an organ specific promoter. In a fourth embodiment, the promoter preferentially directs expression in guard cells. In a fifth embodiment, the nucleic acid encodes a DHAR polypeptide comprising an amino acid sequence substantially identical to SEQ ID NOs: 3, 5, 7, 9, 11, 13, or 15. In a sixth embodiment, the nucleic acid encodes a DHAR polypeptide comprising an amino acid sequence comprising SEQ ID NOs. 3, 5, 7, 9, 11, 13, or 15.

In a sixth aspect, the present invention provides a method of increasing ascorbic acid levels in a plant comprising introducing a construct comprising a promoter operably linked to a nucleic acid encoding a DHAR polypeptide comprising an amino acid sequence at least 80% identical to SEQ ID NO: 1. In one embodiment, the construct is introduced into the plant through a sexual cross. In a second embodiment, the expression cassette is introduced into the plant using *Agrobacterium*. In a third embodiment, the expression cassette is introduced into the plant using biolistics. In a fourth embodiment, the plant is a selected from the group consisting of wheat, tobacco, maize, tomato, rice or spinach. In a fifth embodiment, the method further comprising detecting a plant having increased biomass or yield. In a sixth embodiment, the promoter is an organ specific promoter. In a seventh embodiment, the promoter preferentially directs expression in guard cells. In an eighth embodiment, the nucleic acid encodes a DHAR polypeptide comprising an amino acid sequence substantially identical to SEQ ID NOs: 3, 5, 7, 9, 11, 13, or 15. In a ninth embodiment, the nucleic acid encodes a DHAR polypeptide comprising an amino acid sequence comprising SEQ ID NOs. 3, 5, 7, 9, 11, 13, or 15.

In a seventh aspect, the present invention provides a method of decreasing ascorbic acid levels in a plant comprising introducing a construct comprising a promoter operably linked to a nucleic acid encoding a DHAR polypeptide comprising an amino acid sequence at least 80% identical to SEQ ID NO: 1. In one embodiment, the nucleotide sequence is operably linked to the promoter sequence in an antisense orientation. In a second embodiment, the expression cassette is introduced into the plant through a sexual cross. In a third embodiment, the expression cassette is introduced into the plant using *Agrobacterium*. In a fourth embodiment, the expression cassette is introduced into the plant using biolistics. In a fifth embodiment, the plant is selected from the group consisting of wheat, tobacco, maize, tomato, rice, or spinach. In a sixth embodiment, the method further comprises detecting increased drought tolerance in the plant. In a seventh embodiment, the method further comprises detecting decreased sensitivity to toxins in the plant. In an eight embodiment, the toxin is selected from the group consisting of ozone, nitrous oxide, and sulfur oxide. In a ninth embodiment, the promoter is an organ specific promoter. In a tenth embodiment, the promoter preferentially directs expression in guard cells. In an eleventh embodiment, the nucleic acid encodes a DHAR polypeptide comprising an amino acid sequence substantially identical to SEQ ID NOs: 3, 5, 7, 9, 11, 13, or 15. In a twelfth embodiment, the nucleic acid encodes a DHAR polypeptide comprising an amino acid sequence comprising SEQ ID NOs. 3, 5, 7, 9, 11, 13, or 15.

In an eighth aspect of the present invention, the DHAR polypeptide comprises SEQ ID NO: 1.

In ninth aspect of the present invention, the DHAR polypeptide comprises SEQ ID NO: 3, SEQ ID NO: 5, SEQ ID NO: 7, or SEQ ID NO: 11.

In a tenth aspect, the present invention provides an isolated DHAR polypeptide comprising an amino acid sequence at least 80% identical to SEQ ID NO: 1, wherein the sequence is not SEQ ID NO: 9, SEQ ID NO: 13 or SEQ ID NO: 15. In one embodiment, the DHAR polypeptide further comprises a chloroplast transit peptide. In a second embodiment, the DHAR polypeptide comprises SEQ ID NO: 1. In a third embodiment, the DHAR polypeptide comprises SEQ ID NO: 3, SEQ ID NO: 5, SEQ ID NO: 7, or SEQ ID NO: 11. In a fourth embodiment, the DHAR polypeptide comprises an amino acid sequence substantially identical to SEQ ID NO:s 3, 5, 7, or 11.

In an eleventh aspect, the present invention provides an isolated nucleic acid encoding a DHAR polypeptide comprising a nucleic acid sequence substantially identical to SEQ ID NOS.: 2, 4, 6 or 10.

Definitions

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

The term "promoter" refers to regions or sequence located upstream and/or downstream from the start of transcription and which are involved in recognition and binding of RNA polymerase and other proteins to initiate transcription. A "plant promoter" is a promoter capable of initiating transcription in plant cells.

The term "plant" includes whole plants, shoot vegetative organs and/or structures (e.g. leaves, stems and tubers), roots, flowers and floral organs (e.g. bracts, sepals, petals, stamens, carpels, anthers), ovules (including egg and central cells), seed (including zygote, embryo, endosperm, and seed coat), fruit (e.g., the mature ovary), seedlings, plant tissue (e.g. vascular tissue, ground tissue, and the like), cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety).

A polynucleotide "exogenous to" an individual plant is a polynucleotide which is introduced into the plant by any means other than by a sexual cross. Examples of means by which this can be accomplished are described below, and include Agrobacterium-mediated transformation, biolistic methods, electroporation, and the like. Such a plant containing the exogenous nucleic acid is referred to here as a T1 (e.g. in *Arabidopsis* by vacuum infiltration) or R0 (for plants regenerated from transformed cells in vitro) generation transgenic plant. Transgenic plants that arise from sexual cross or by selfing are descendants of such a plant.

An "DHAR nucleic acid" or "DHAR polynucleotide sequence" of the invention is a subsequence or full length polynucleotide sequence which, encodes a DHAR polypeptide and its complement, e.g., SEQ ID NOS: 2, 4, 6 or 8. DHAR gene products of the invention (e.g., mRNAs or polypeptides) are characterized by the ability to modulate ASC levels and thereby control such phenotypes as Vitamin C content, enhanced biomass, stomatal closing, stomatal opening, whole plant transpirational water loss during drought, increased $CO_2$ assimilation, decreased toxin sensitivity. A DHAR polynucleotide of the invention typically comprises a coding sequence at least about 250 nucleotides to about 2000 nucleotides in length. Usually the DHAR nucleic acids of the invention are from about 400 to about 1500 nucleotides.

A DHAR nucleic acid of the present invention may also include a chloroplast transit signal sequence. Chloroplast transit signal sequences encode chloroplast transit peptides and initiate DHAR polypeptide translocation into the chloroplast. Chloroplast transit peptides are well known in the art and can be identified by standard means, e.g., analysis with ChloroP (Emmanuelsson et al., *Protein Sci.* 8:978-984 or Schein et al., *Nucleic Acids Res,* 15;29(16)E82 (2001)). The site at which the transit peptide is cleaved from a DHAR polypeptide can be determined by known methods, e.g., comparing the predicted amino acid sequence of the transit sequence with the amino-terminal of a purified chloroplast DHAR polypeptide. An exemplary transit peptide sequence can be found in Shimaoka et al. *Plant Cell Physiol.,* 41(10): 1110-1118(2000).

A consensus sequence is a minimum nucleotide or amino acid sequence found to be common in genes or proteins from different organisms. Typically, the genes or proteins are associated with a specific function. The DHAR consensus sequence of the present invention is a minimum amino acid sequence common in DHAR polypeptides. The DHAR consensus sequence of the present invention was derived from the protein sequences of the following DHAR polypeptides: wheat, rice, tomato, maize, tobacco, and *Arabidopsis*. Standard methodologies were used to align known DHAR amino acid sequences to create the DHAR consensus sequence.

In the case of both expression of transgenes and inhibition of endogenous genes (e.g., by antisense, or co-suppression) one of skill will recognize that the inserted polynucleotide sequence need not be identical, but may be only "substantially identical" to a sequence of the gene from which it was derived. As explained below, these substantially identical variants are specifically covered by the term DHAR nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "DHAR nucleic acid", "DHAR polynucleotide" and their equivalents. In addition, the terms specifically include those full length sequences substantially identical (determined as described below) with a DHAR polynucleotide sequence and that encode proteins that retain the function of the DHAR polypeptide (e.g., resulting from conservative substitutions of amino acids in the DHAR polypeptide).

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11-17 (1988) e.g., as implemented in the program PC/GENE (Intelligenetics, Mountain View, Calif., USA).

The phrase "substantially identical," in the context of two nucleic acids or polypeptides, refers to a sequence or subsequence that has at least 25% sequence identity with a reference sequence. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 90%, 95%, or 99%, compared to a reference sequence using the programs described herein; preferably, BLAST using standard parameters, as described below. This definition also refers to the complement of a test sequence, when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., J. Mol. Biol. 2 15:403-410 (1990). Software for performing BLAST analyses is publicly available through the National Center for Biotechnology Information This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSULM62 scoring matrix (see Henikoff & Henikoff, Proc. Nati. Acad. Sci. USA 89:10915 (1989)) alignments (B) of 50, expectation (E) of 10, M=5, N=4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about 10–5, and most preferably less than about 10–20.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). ps (see, e.g., Creighton, Proteins (1984)

One indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, highly stringent conditions are selected to be about 5–10° C. lower than the thermal melting point (Tm) for the specific sequence at a defined ionic strength pH. Low stringency conditions are generally selected to be about 15–30° C. below the Tm. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

In the present invention, genomic DNA or cDNA comprising DHAR nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., an RNA gel or DNA gel blot hybridization analysis.

DETAILED DESCRIPTION OF THE INVENTION

The present invention provides novel isolated nucleic acids and polypeptides that can be used to modulate (e.g., increase or decrease) ASC levels in plants. Recombinant constructs incorporating the nucleic acids of the invention operably linked to various promoters are used to generate transformed plant cells and transgenic plants.

The invention provides both compositions and means to both increase or decrease ascorbic acid levels in plants. An increase in the expression of DHAR, the enzyme responsible for regenerating ascorbic acid from its oxidized form results in an increase in the level of ascorbic acid in plants. The DHAR polynucleotides of the present invention therefore can be used to create transgenic plants with higher or lower Vitamin C content. Ascorbic acid, in its role as an antioxidant, scavenges active oxygen species in plants. The DHAR polynucleotides of the present invention therefore can also be used to confer broad protection against oxidative stresses in plants. One role of ASC is to scavenge hydrogen peroxide in plant guard cells. The intracellular concentration of hydrogen peroxide in guard cells controls stomatal opening and closings. Increased levels of hydrogen peroxide cause stomatal closures whereas decreased levels cause stomatal openings. Closed stomatas protect the plant against environmental conditions such as aerosolized toxins and drought (transpiration occurs through the stomata). Opened stomatas allow for greater exchange between the plant and the outside environment. Plants with increased ASC levels display increased carbon fixation activity and enhanced biomass. The DHAR polynucleotides of the present invention therefore can be used to protect plants against environmental conditions or to provide for a greater exchange between plants and the environment.

Isolation of Nucleic Acids of the Invention

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989) or *Current Protocols in Molecular Biology*, Volumes 1–3, John Wiley & Sons, Inc. (1994–1998).

Using the sequences provided here, the isolation of DHAR nucleic acids the sequence provided here may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as flowers, and a cDNA library which contains the DHAR gene transcript is prepared from the mRNA. Alternatively, cDNA may be prepared from mRNA extracted from other tissues in which DHAR genes or homologs are expressed.

The cDNA or genomic library can then be screened using a probe based upon the sequence of a cloned DHAR gene disclosed here. Probes may be used to hybridize with genomic DNA or cDNA sequences to isolate homologous genes in the same or different plant species. Alternatively, antibodies raised against a DHAR polypeptide can be used to screen a mRNA expression library.

Alternatively, the nucleic acids of interest can be amplified from nucleic acid samples using amplification techniques. For instance, polymerase chain reaction (PCR) technology can be used to amplify the sequences of the DHAR genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see PCR Protocols: A Guide to Methods and Applications. (Innis, M, Gleaned, D., Sninsky, J. and White, T., eds.), Academic Press, San Diego (1990).

Polynucleotides may also be synthesized by well-known techniques as described in the technical literature. See, e.g., Carruthers et al., *Cold Spring Harbor Symp. Quant. Biol.*, 47:411–418 (1982), and Adams et al., *J. Am. Chem. Soc.*, 105:661 (1983). Double stranded DNA fragments may then be obtained either by synthesizing the complementary strand and annealing the strands together under appropriate conditions, or by adding the complementary strand using DNA polymerase with an appropriate primer sequence.

DHAR nucleic acids of interest may also be identified by searching nucleic acid databases, e.g., EST databases and identifying sequences with high similarity to a known DHAR nucleic acid sequence. Once a candidate DHAR nucleic acid or polynucleotide sequence of the invention has been identified, standard methods can be used to determine if the putative nucleic acid is a DHAR nucleic acid of the invention. Methods of assaying for DHAR activity are known in the art, e.g., see example 1 and Hossain et al., *Plant Cell Physiol.* 25, 85–92.

Increasing DHAR Activity or Expression

Any of a number of means well known in the art can be used to increase DHAR activity in plants. Enhanced expression is useful for increasing levels of ASC in plants. For example, enhanced expression can be used to increase antioxidant activity and Vitamin C content in plants. Enhanced expression can be used to modulate the stomatal aperture. Increased levels of ASC in plants induces stomatal openings by scavenging hydrogen peroxide. Open stomatas support a greater exchange between plants and the environment providing for greater $CO_2$ assimilation and enhanced plant biomass.

Increasing DHAR Gene Expression

Isolated sequences prepared as described herein can be used to introduce expression of a particular DHAR nucleic acid to increase endogenous gene expression using methods well known to those of skill in the art.

One of skill will recognize that the polypeptides encoded by the genes of the invention, like other proteins, have different domains that perform different functions. Thus, the gene sequences need not be full length, so long as the desired functional domain of the protein is expressed. The distinguishing features of DHAR polypeptides are discussed below.

Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

Other Means for Increasing DHAR Activity

One method to increase DHAR expression is to use "activation mutagenesis" (see, e.g. Hiyashi et al. *Science*, 258:1350–1353 (1992)). In this method an endogenous DHAR gene can be modified to be expressed constitutively, ectopically, or excessively by insertion of T-DNA sequences that contain strong/constitutive promoters upstream of the endogenous DHAR gene. As explained below, preparation of transgenic plants overexpressing DHAR can also be used to increase DHAR expression. Activation mutagenesis of the endogenous DHAR gene will give the same effect as overexpression of the transgenic DHAR nucleic acid in transgenic plants. Alternatively, an endogenous gene encoding an enhancer of DHAR activity or expression of the endogenous DHAR gene can be modified to be expressed by insertion of T-DNA sequences in a similar manner and DHAR activity can be increased.

Another strategy to increase DHAR expression can be the use of dominant hyperactive mutants of DHAR by expressing modified DHAR transgenes. For example expression of modified DHAR with a defective domain that is important for interaction with a negative regulator of DHAR activity can be used to generate dominant hyperactive DHAR proteins. Alternatively, expression of truncated DHAR proteins which have only a domain that interacts with a negative regulator can titrate the negative regulator and thereby increase endogenous DHAR activity. Use of dominant mutants to hyperactivate target genes is described in Mizukami et al., *Plant Cell*, 8:831–845 (1996).

Inhibition of DHAR Activity or Gene Expression

As explained above, DHAR activity is important in controlling ASC levels. In some embodiments, ASC levels are decreased, thereby increasing hydrogen peroxide levels and inducing stomatal closures. Inhibition of DHAR gene expression activity can be used, for instance, to increase drought tolerance by decreasing transpiration in transgenic plants or to decrease sensitivity to toxins by barring entry of toxins in transgenic plants. Targeted expression of DHAR nucleic acids that inhibit endogenous gene expression (e.g., antisense or co-suppression) can be used for this purpose.

Inhibition of DHAR Gene Expression

The nucleic acid sequences disclosed here can be used to design nucleic acids useful in a number of methods to inhibit DHAR or related gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque *Plant Sci.* (*Limerick*) 105:125–149 (1995); Pantopoulos In *Progress in Nucleic Acid Research and Molecular Biology*, Vol. 48. Cohn, W. E. and K. Moldave (Ed.). Academic Press, Inc.: San Diego, Calif., USA; London, England, UK. p. 181–238; Heiser et al. *Plant Sci.*, (Shannon) 127:61–69 (1997)) and by preventing the accumulation of mRNA which encodes the protein of interest, (see, Baulcombe, *Plant Mol. Bio.*, 32:79–88 (1996); Prins and Goldbach, *Arch. Virol.*, 141:2259–2276 (1996); Metzlaff et al. *Cell*, 88 845–854 (1997), Sheehy et al., *Proc. Nat. Acad. Sci. USA*, 85:8805–8809 (1988), and Hiatt et al., U.S. Pat. No. 4,801,340).

The nucleic acid segment to be introduced generally will be substantially identical to at least a portion of the endogenous DHAR gene or genes to be repressed. The sequence, however, need not be perfectly identical to inhibit expression. The vectors of the present invention can be designed such that the inhibitory effect applies to other genes within a family of genes exhibiting identity or substantial identity to the target gene.

For antisense suppression, the introduced sequence also need not be full length relative to either the primary transcription product or fully processed mRNA. Generally, higher identity can be used to compensate for the use of a shorter sequence. Furthermore, the introduced sequence need not have the same intron or exon pattern, and identity of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 3500 nucleotides is especially preferred.

A number of gene regions can be targeted to suppress DHAR gene expression. The targets can include, for instance, the coding regions, introns, sequences from exon/intron junctions, 5' or 3' untranslated regions, and the like.

Another well known method of suppression is sense co-suppression. Introduction of nucleic acid configured in the sense orientation has been recently shown to be an effective means by which to block the transcription of target genes. For an example of the use of this method to modulate expression of endogenous genes (see, Assaad et al. *Plant Mol. Bio.*, 22:1067–1085 (1993); Flavell, Proc. *Natl. Acad. Sci. USA*, 91:3490–3496 (1994); Stam et al. *Annals Bot.*, 79:3–12 (1997); Napoli et al., *The Plant Cell*, 2:279–289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. In one embodiment, the introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. In another embodiment, the introduced sequence will have a region of 21 nucleotides with 100% identity to the endogenous sequence intended to be repressed. As with antisense regulation, the effect should apply to any other proteins within a similar family of genes exhibiting identity or substantial identity.

For co-suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using co-suppression technologies.

Oligonucleotide-based triple-helix formation can also be used to disrupt DHAR gene expression. Triplex DNA can inhibit DNA transcription and replication, generate site-specific mutations, cleave DNA, and induce homologous recombination (see, e.g., Havre and Glazer, *J. Virology*, 67:7324–7331 (1993); Scanlon et al., *FASEB J.*, 9:1288–1296 (1995); Giovannangeli et al., *Biochemistry*, 35:10539–10548 (1996); Chan and Glazer, *J. Mol. Medicine* (*Berlin*), 75:267–282 (1997)). Triple helix DNAs can be used to target the same sequences identified for antisense regulation.

Transposon insertions or tDNA insertions can be used to inhibit expression of DHAR genes. Standard methods are known in the art. Catalytic RNA molecules or ribozymes can also be used to inhibit expression of DHAR genes. For example, it is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Zhao and Pick, *Nature*, 365:448–451 (1993); Eastham and Ahlering, *J. Urology*, 156:1186–1188 (1996); Sokol and Murray, *Transgenic Res.*, 5:363–371 (1996); Sun et al., *Mol. Biotechnology*, 7:241–251 (1997); and Haseloff et al., *Nature*, 334:585–591 (1988).

Modification of Endogenous DHAR Genes

Methods for introducing genetic mutations described above can also be used to select for plants with decreased DHAR expression.

DHAR activity may be modulated by eliminating the proteins that are required for DHAR cell-specific gene expression. Thus, expression of regulatory proteins and/or the sequences that control DHAR gene expression can be modulated using the methods described here.

Another strategy is to inhibit the ability of a DHAR protein to interact with itself or with other proteins. This can be achieved, for instance, using antibodies specific to DHAR. In this method cell-specific expression of DHAR-specific antibodies is used to inactivate functional domains through antibody: antigen recognition (see, Hupp et al., *Cell*, 83:237–245 (1995)). Interference of activity of a DHAR interacting protein(s) can be applied in a similar fashion. Alternatively, dominant negative mutants of DHAR can be prepared by expressing a transgene that encodes a truncated DHAR protein. Use of dominant negative mutants to inactivate target genes in transgenic plants is described in Mizukami et al., *Plant Cell*, 8:831–845 (1996).

Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.*, 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill. Such genes include for example, ACT11 from *Arabidopsis* (Huang et al. *Plant Mol. Biol.*, 33:125–139 (1996)), Cat3 from *Arabidopsis* (GenBank No. U43147, Zhong et al., *Mol. Gen. Genet.*, 251:196–203 (1996)), the gene encoding stearoyl-acyl carrier protein desaturase from *Brassica napus* (Genbank No. X74782, Solocombe et al. *Plant Physiol.*, 104:1167–1176 (1994)), GPc1 from maize (GenBank No. X15596, Martinez et al. *J. Mol. Biol*, 208:551–565 (1989)), and Gpc2 from maize (GenBank No. U45855, Manjunath et al., *Plant Mol. Biol.*, 33:97–112 (1997)).

Alternatively, the plant promoter may direct expression of the DHAR nucleic acid in a specific tissue, organ or cell type (i.e. tissue-specific promoters, organ-specific promoters) or may be otherwise under more precise environmental or developmental control (i.e. inducible promoters). Examples of environmental conditions that may effect transcription by inducible promoters include anaerobic conditions, elevated temperature, the presence of light, or sprayed with chemicals/hormones. One of skill will recognize that an organ-specific promoter may drive expression of operably linked sequences in organs other than the target organ. Thus, as used herein an organ-specific promoter is one that drives expression preferentially in the target organ, but may also lead to some expression in other organs as well.

A number of tissue-specific promoters can also be used in the invention. For instance, promoters that direct expression of nucleic acids in guard cells are useful for conferring drought tolerance. One such particularly preferred promoter is KAT1, which has been shown in transgenic plants to drive expression primarily in guard cells (see, Nakamura, R., et al., *Plant Physiol.*, 109:371–374 (1995). Another particularly preferred promoter is the truncated 0.3 kb 5' proximal fragment of potato ADP-glucose pyrophosphorylase, which has been shown to drive expression exclusively in guard cells of transgenic plants. See, e.g., Muller-Rober, B., et al., *Plant Cell*, 6:601–612 (1994).

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, (G418, bleomycin, hygromycin, or herbicide resistance, such as resistance to chlorosulfuron or Basta. The present invention also provides promoter sequences from the DHAR gene (SEQ ID NO: 3), which can be used to direct expression of the DHAR coding sequence or heterologous sequences in desired tissues.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using biolistics, e.g., DNA particle bombardment.

Microinjection techniques are known in the art and well described in the scientific and patent literature. The introduction of DNA constructs using polyethylene glycol precipitation is described in Paszkowski et al. *Embo J.*, 3:27 17–2722 (1984). Electroporation techniques are described in Fromm et al. *Proc. Natl. Acad. Sci. USA*, 82:5824 (1985). Biolistic transformation techniques are described in Klein et al. *Nature*, 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science*, 233:496–498 (1984), and Fraley et al. *Proc. Natl. Acad. Sci. USA*, 80:4803 (1983) and Gene Transfer to Plants, Potrykus, ed. (Springer-Verlag, Berlin 1995).

Transformed plant cells which are derived by any of the above transformation techniques can be cultured to regenerate a whole plant which possesses the transformed genotype and thus the desired phenotype such as decreased farnesyltransferase activity. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al., *Ann. Rev, of Plant Phys.*, 38:467–486 (1987).

The nucleic acids of the invention can be used to confer desired traits on essentially any plant. Thus, the invention has use over a broad range of plants, including species from the genera *Anacardium, Arachis, Asparagus, Atropa, Avena, Brassica, Chlamydomonas, Chlorella, Citrus, Citrullus, Capsicum, Carthamus, Cocos, Coffea, Cucumis, Cucurbita, Cyrtomium, Daucus, Elaeis, Fragaria, Glycine, Gossypium, Helianthus, Heterocallis, Hordeum, Hyoscyamus, Lactuca, Laminaria, Linum, Lolium, Lupinus, Lycopersicon, Macrocystis, Malus, Manihot, Majorana, Medicago, Nereocystis, Nicotiana, Olea, Oryza, Osmunda, Panieum, Pannesetum, Persea, Phaseolus, Pistachia, Pisum, Pyrus, Polypodium, Prunus, Pteridium, Raphanus, Ricinus, Secale, Senecio, Sinapis, Solanum, Sorghum, Theobromus, Trigonella, Triticum, Vicia, Vitis, Vigna*, and *Zea*. In particular, the invention is useful with any plant with guard cells.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Using known procedures one of skill can screen for plants of the invention by detecting the increase or decrease of DHAR mRNA or protein in transgenic plants. Means for detecting and quantifying mRNAs or proteins are well known in the art, e.g., Northern Blots, Western Blots or activity assays. The plants of the invention can also be identified by detecting the desired phenotype. For instance, measuring stomatal apertures, Vitamin C content, drought tolerance, toxin tolerance and rates of $CO_2$ assimilation using methods as described below.

Detection of Transgenic Plants of the Invention

After preparation of the expression cassettes of the present invention and introduction of the cassettes into a plant, the resultant transgenic plants can be assayed for the phenotypical characteristics associated with increased or decreased DHAR expression. For example, after introduction of the cassette into a plant, the plants are screened for the presence of the transgene and crossed to an inbred or hybrid line. Progeny plants are then screened for the presence of the transgene and self-pollinated. Progeny from the self-pollinated plants are grown. The resultant transgenic plants can be assayed for increased drought tolerance, decreased sensitivity to toxins, increased cellular Vitamin C content, and increased $CO_2$ assimilation. For example, a transgenic plant can be assayed for increased drought tolerance. Methods for assaying for increased drought tolerance are known and include measuring transpiration rate of transgenic plants, stomatal conductance, rate of water loss in a detached leaf assay or examining leaf turgor. Transgenic plants with decreased transpiration rates, for example, have increased drought tolerance. In another embodiment of the present invention, transgenic plants can be assayed for decreased sensitivity to toxins using known methods. In one method, for example, transgenic plants overexpressing DHAR, transgenic plants co-suppressed for DHAR, and control plants are exposed to 160 parts per billion (ppb) ozone for 3 days, 7 hours a day and subsequently examined. Leaves of plants with sensitivity to toxins will show ozone induced damages such as necrosis, while leaves with decreased sensitivity will show less or no ozone-induced damage. In other embodiments, transgenic plants can be examined for enhanced biomass, yield and Vitamin C (ASC) content using standard techniques.

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

EXAMPLE 1

Overexpression of DHAR

A full-length wheat DHAR cDNA was isolated following the screening of a wheat seedling cDNA expression library using anti-wheat DHAR antiserum. A full-length tobacco DHAR cDNA was isolated following the screening a tobacco seedling cDNA library using the wheat DHAR cDNA as the probe. Full-length ESTs for rice, tomato, and *Arabidopsis* were identified in GenBank. The sequence for a full-length maize DHAR was constructed from two partial ESTs (i.e., AW258053 and BE552888) that were identical in the region of overlap. The wheat DHAR cDNA was introduced into the *E. coli* expression vectors, pET19b and pET 11 (Novagen), which allowed expression of recombinant wheat DHAR with or without an N-terminal His-tag, respectively. The His-tagged wheat DHAR cDNA construct was introduced under the control of the CaMV 35S promoter in the binary vector, pBI101 (Clontech Laboratories, Inc.). The resulting construct was introduced into *Agrobacterium tumefaciens* strain LBA4404 which was used essentially as described (17) to obtain tobacco (*N. tabacum*, cv. Xanthi) transformants expressing wheat DHAR.

To generate maize overexpressing the wheat DHAR, the DHAR coding region (without an N-terminal His-tag) was placed under the control of the maize ubiquitin (Ub) promoter in the vector, pACH18 (18). DHAR was also placed under the control of the maize Shrunken 2 (Sh2) promoter (amplified as a 1.5 kbp fragment from B73) which had been substituted for the ubiquitin promoter in pACH18. Each construct was introduced into embryogenic A188×B73 (HiII) maize callus using particle bombardment as described (19). Co-transformation with the bar gene provided bialaphos selection for the isolation of transformed callus used for regeneration (20). Regenerants containing the Sh2-DHAR or Ub-DHAR constructs were identified using PCR and DHAR expression confirmed by activity assay and Western analysis using anti-wheat DHAR antiserum. $T_0$ plants were crossed with HiII, transgene-containing progeny identified, and the $T_1$ plants selfed.

DHAR was purified to homogeneity from 10 day old wheat leaves and was used to raise anti-DHAR antiserum in rabbits. For Western analysis, a membrane containing the protein of interest was blocked for 30 min in TPBS (0.1% TWEEN 20, 13.7 mm NaCl, 0.27 mm KCl, 1 mm $Na_2HPO_4$, 0.14 mm $KH_2PO_4$) with 5% reconstituted dry milk and incubated with anti-wheat DHAR (diluted 1:1000) in TPBS with 1% milk for 1.5 hrs. The blots were then washed with TPBS, incubated with goat anti-rabbit-horseradish peroxidase a antibody (Southern Biotechnology) diluted 1:5000 to 1:10,000 for 1 hr, and DHAR detected using chemilumensence (Amersham Corp).

DHAR activity was assayed as described in Hossain et al., *Plant Cell physiol.* 25, 85–92(1984). Soluble protein was extracted from tobacco leaves or maize kernels ground in liquid nitrogen before grinding in extraction buffer (50 mM Tris-HCl pH 7.4, 100 mM NaCl, 2 mM EDTA, 1 mM $MgCl_2$) and centrifugation twice at 13,000 rpm for 5 min to remove cell debris. Protein concentration was determined as described (22). DHAR activity was assayed from an equal amount of protein by adding extract in a reaction containing 50 mM $K_2HPO_4/KH_2PO_4$ pH 6.5, 0.5 mM DHA, and 1 mM GSH. The activity of DHAR was followed by an increase in absorbance at 265 nm.

Ascorbic acid was determined as described in Foyer et al., *Planta*, 157, 239–244. Fresh leaves were ground in 2.5 M $HClO_4$ and centrifuged at 13,000 rpm for 10 min to remove cell debris. Two volumes of 1.25 M $Na_2CO_3$ were added to the supernatant to neutralize it and the sample was centrifuged at 13,000 rpm for 5 min. Ascorbate was measured from the supernatant immediately by adding 100 ml of the sample to a reaction containing 895 ml 100 mM $K_2HPO_4/KH_2PO_4$ pH 5.6. The amount of ascorbate was determined by the change in absorbance at 265 nm before and after the addition of 0.25 unit ascorbate oxidase to the reaction. A range of ascorbate concentrations was assayed to serve as standards. The total amount of reduced and oxidized ascorbic acid (i.e., AsA and DHA) was determined by reducing DHA to AsA (in a reaction containing 100 mM $K_2HPO_4/KH_2PO_4$ pH 6.5, 2 mM GSH, and 0.1 mg recombinant wheat DHAR protein incubated at 25° C. for 20 min) prior to measuring ascorbic acid. The amount of DHA was determined as the difference between these two assays. GSH and GSSG were determined from fresh leaves as described (24).

DHAR Activity Declines With Leaf Age

Prior to an attempt to increase DHAR expression, it was necessary to determine the expression profile of DHAR during leaf development. For this purpose, tobacco was selected as a model species possessing a large leaf size that permits biochemical analysis of leaves from young and expanding to those that are pre-senescent. DHAR activity and protein was measured in individual leaves from an adult plant containing approximately 20 leaves in which the inflorescence had not yet emerged. DHAR activity was highest in young, expanding leaves and in the first fully-expanded leaf in which photosynthesis was highest. The level of DHAR declined thereafter as a function of leaf age. The decrease in DHAR activity was accompanied by a decrease in DHAR protein although to a lesser extent suggesting regulation of DHAR enzyme activity. Moreover, the decrease in DHAR activity preceded the onset of visible signs of leaf senescence, e.g., the loss of chlorophyll. These data illustrate that expression of DHAR activity and DHAR protein correlate with leaf age and function.

Isolation of cDNAs Encoding DHAR

With the exception of rice and spinach, DHAR cDNAs from plant species have not been reported. Consequently, cDNAs encoding DHAR were isolated from wheat and tobacco cDNA libraries. A full-length cDNA was isolated from a wheat cDNA library using anti-DHAR antiserum and this cDNA was used to screen a tobacco cDNA library. Full-length ESTs encoding DHAR were identified from tomato, *Arabidopsis*, and rice, and a full-length maize EST was reconstructed from two partial ESTs. The rice EST identified in this study was identical to that previously reported (see Urano et al., *FEBS Lett.*, 4, 107–111). Comparison of the amino acid sequence predicted from each cDNA or EST revealed that DHAR is conserved in molecular weight (23, 358 Da for the wheat ortholog) and composition among plants (FIG. 2). Expression of wheat DHAR in *E. coli* as a N-terminal His-tagged protein exhibited substantial DHAR activity (9.1 mmol/min/mg) and was approximately 40% as active as wheat DHAR without a His-tag (23 mmol/min/mg) when an equal amount of each protein from *E. coli* extract was assayed.

Overexpression of DHAR in Leaves

In order to generate tobacco with altered DHAR expression, the His-tagged wheat DHAR cDNA was placed under the control of the CaMV 35S promoter in the binary vector, pBI101, which was subsequently introduced into tobacco. Regenerants screened for expression of wheat DHAR identified multiple individuals that overexpressed the transgene. Analysis of DHAR expression from leaves of three representative transgenic $T_1$ progeny revealed substantial overexpression of the wheat DHAR transgene. The presence of the N-terminal His-tag resulted in a transgenic DHAR of larger molecular weight that allowed the extent of its expression to be distinguished from expression of the endogenous tobacco DHAR. The expression of wheat DHAR appeared as two bands where the lower one corresponds to the recombinant His-tagged form, suggesting that the upper band may be modified in a way that retards its migration. Overexpression of the wheat DHAR transgene did not alter expression of the endogenous tobacco DHAR. Overexpression of the wheat DHAR protein was accompanied by a substantial increase in DHAR activity in the transgenic leaves. Because DHAR expression declines with increasing leaf age, DHAR activity was measured in young, mature, and pre-senescent leaves of three transgenic individuals. As observed for the endogenous DHAR, the level of wheat DHAR activity declined with leaf age, however, overexpression of wheat DHAR resulted in up to an 11-fold increase in DHAR activity in young, expanding leaves, up to a 13-fold increase in mature leaves, and up to a 32-fold increase in pre-senescent leaves relative to control tobacco. Expression of the wheat DHAR did not affect the rate of growth or timing of flowering of the transgenic tobacco.

Increasing DHAR Activity Results in Increased Ascorbic acid and Glutathione Content To determine the metabolic consequences of DHAR overexpression, the level of its substrate, i.e., DHA, and its product, i.e., AsA, were measured in DHAR-overexpressing and control plants. Because DHAR activity declined with leaf age, the level of AsA was measured in young, mature, and pre-senescent leaves. The level of AsA was elevated up to 2.4-fold in young, expanding leaves, up to 3.9-fold in mature leaves, and up to 2.2-fold in pre-senescent leaves. Concomitant with the increase in ascorbic acid, a decrease in DHA was detected in young, expanding leaves which, together with the increase in AsA, resulted in a substantial change in the redox state from a ratio of AsA to DHA from 1.5 in control leaves to 4.8 in leaves overexpressing DHAR. Increases in the AsA to DHA ratio were observed in older leaves as well.

Because GSH is used as the reductant by DHAR to reduce DHA to AsA, the level of reduced and oxidized glutathione was measured in the same leaves. The level of GSH was elevated up to 2.6-fold in young, expanding leaves, up to 2.0-fold in mature leaves, and up to 1.9-fold in pre-senescent leaves (FIG. 5). The redox status of glutathione increased in young leaves but was little changed in older leaves. Consequently, the overexpression of wheat DHAR resulted in an elevation in the absolute level of ascorbic acid and reduced glutathione as well as a substantial change in the redox state of leaves.

To examine whether increasing the expression of DHAR in a non-photosynthetic organ of a crop species would result in an increase in ascorbic acid content, the wheat DHAR coding region (without an N-terminal His-tag) was placed under the control of the maize ubiquitin (Ub) promoter in the vector, pACH18 (18). DHAR was also placed under the control of the maize Shrunken 2 (Sh2) promoter which had been substituted for the Ub promoter in pACH18. Regenerants containing the Sh2-DHAR or Ub-DHAR constructs following particle bombardment of embryogenic Hill callus were identified using PCR and confirmed by DHAR activity assay as well as Western analysis. $T_1$ progeny from a cross between $T_0$ plants and Hill were then grown and progeny from self-pollinated $T_1$ plants used for ascorbic acid measurements. Ascorbic acid from grain of plants containing just the Ub-DHAR construct, just the Sh2-DHAR construct, or both constructs was measured. Grain not containing either transgene had little endogenous DHAR activity and protein, suggesting that recycling of ascorbic acid may not occur at a high rate in maize grain. In grain expressing wheat DHAR (calculated MW of 23,358 kD), the transgenic protein co-migrated with the endogenous maize DHAR (calculated MW of 23,328 kD). High overexpression of DHAR resulted in up to a 2.7-fold increase in the level of ascorbic acid. This increase was observed for plants expressing DHAR from the Ub and/or Sh2 promoters. Expression of DHAR to moderate levels in each transgenic line resulted in smaller increases in ascorbic acid content. These data demonstrate that the level of ascorbic acid can be increased in a non-photosynthetic organ as well as in a photosynthetic organ such as leaves.

What is claimed is:

1. An isolated nucleic acid encoding a dehydroascorbate reductase (DHAR) polypeptide comprising an amino acid sequence at least 95% identical to SEQ ID NO:3.

2. A recombinant expression cassette comprising a promoter operably linked to a nucleic acid encoding a DHAR polypeptide comprising an amino acid sequence at least 95% identical to SEQ ID NO:3.

3. The expression cassette of claim 2, further comprising a chloroplast transit signal sequence operatively linked to the polypeptide.

4. The expression cassette of claim 2, wherein the DHAR polypeptide comprises SEQ ID NO:3.

5. The expression cassette of claim 2, wherein the nucleic acid is operably linked to the promoter in an antisense orientation.

6. The expression cassette of claim 2, wherein the promoter is a constitutive promoter.

7. The expression cassette of claim 2, wherein the promoter is an organ specific promoter.

8. The expression cassette of claim 7, wherein the promoter preferentially directs expression in guard cells.

9. A transgenic plant comprising a recombinant expression cassette comprising a plant promoter operably linked to a nucleic acid encoding a DHAR polypeptide comprising an amino acid sequence at least 95% identical to SEQ ID NO:3.

10. The plant of claim 9, wherein the nucleic acid is operably linked to the promoter in an antisense orientation.

11. The plant of claim 9, wherein the promoter is an organ specific promoter.

12. The plant of claim 11, wherein the promoter preferentially directs expression in guard cells.

13. A method of increasing ascorbic acid levels in a plant, the method comprising introducing into a plant the expression cassette of claim 2, thereby increasing ascorbic acid levels in the plant.

14. A method of increasing biomass of a plant, the method comprising introducing into a plant the expression cassette of claim 2, wherein ascorbic acid levels are increased in the plant, and wherein biomass of the plant is increased.

15. The method of claim 13 or 14, wherein the construct is introduced into the plant through a sexual cross.

16. The method of claim 13 or 14, wherein the expression cassette is introduced into the plant using Agrobacterium.

17. The method of claim 13 or 14, wherein the expression cassette is introduced into the plant using biolistics.

18. The method of claim 13 or 14, wherein the promoter is an organ specific promoter.

19. The method of claim 18, wherein the promoter preferentially directs expression in guard cells.

20. A method of decreasing ascorbic acid levels in a plant, the method comprising introducing into a plant the expression cassette of claim 2, thereby decreasing ascorbic acid levels in the plant.

21. A method of increasing drought tolerance in a plant, the expression cassette of claim 2, wherein ascorbic acid levels are decreased in the plant, and wherein drought tolerance is increased in the plant.

22. A method of decreasing sensitivity to aerosolized toxins in a plant, the expression cassette of claim 2, wherein ascorbic acid levels are decreased in the plant, and wherein sensitivity to aerosolized toxins is decreased in the plant.

23. The method of claim 20, 21 or 22, wherein the nucleic acid is operably linked to the promoter in an antisense orientation.

24. The method of claim 20, 21 or 22, wherein the expression cassette is introduced into the plant through a sexual cross.

25. The method of claim 20, 21 or 22, wherein the expression cassette is introduced into the plant using Agrobacterium.

26. The method of claim 20, 21 or 22, wherein the expression cassette is introduced into the plant using biolistics.

27. The method of claim 20, the method further comprising detecting increased drought tolerance in the plant.

28. The method of claim 20, 21 or 22, wherein the promoter is an organ specific promoter.

29. The method of claim 28, wherein the promoter preferentially directs expression in guard cells.

* * * * *

SEQUENCE LISTING

```
<160> NUMBER OF SEQ ID NOS: 15

<210> SEQ ID NO 1
<211> LENGTH: 214
<212> TYPE: PRT
<213> ORGANISM: Artificial Sequence
<220> FEATURE:
<223> OTHER INFORMATION: Description of Artificial
      Sequence:dehydroascorbate reductase (DHAR)
      consensus sequence
<220> FEATURE:
<221> NAME/KEY: MOD_RES
<222> LOCATION: (1)..(4)
<223> OTHER INFORMATION: Xaa = any amino acid
<220> FEATURE:
<221> NAME/KEY: MOD_RES
<222> LOCATION: (5)
<223> OTHER INFORMATION: Xaa = acidic amino acid = Arg or Lys
<220> FEATURE:
<221> NAME/KEY: MOD_RES
<222> LOCATION: (6)
<223> OTHER INFORMATION: Xaa = bulky aliphatic amino acid = Ile, Leu,
      Val or Met
<220> FEATURE:
<221> NAME/KEY: MOD_RES
<222> LOCATION: (10)
<223> OTHER INFORMATION: Xaa = hydrophobic amino acid = Ile, Leu, Val,
      Met, Phe, Tyr, Trp, Cys or Ala
<220> FEATURE:
<221> NAME/KEY: MOD_RES
<222> LOCATION: (12)
<223> OTHER INFORMATION: Xaa = hydrophobic amino acid = Ile, Leu, Val,
      Met, Phe, Tyr, Trp, Cys or Ala
<220> FEATURE:
<221> NAME/KEY: MOD_RES
<222> LOCATION: (14)
<223> OTHER INFORMATION: Xaa = any amino acid
<220> FEATURE:
<221> NAME/KEY: MOD_RES
<222> LOCATION: (16)..(17)
<223> OTHER INFORMATION: Xaa = any amino acid
<220> FEATURE:
<221> NAME/KEY: MOD_RES
<222> LOCATION: (27)
<223> OTHER INFORMATION: Xaa = hydrophobic amino acid = Ile, Leu, Val,
      Met, Phe, Tyr, Trp, Cys or Ala
<220> FEATURE:
<221> NAME/KEY: MOD_RES
<222> LOCATION: (36)
```

```
<223> OTHER INFORMATION: Xaa = bulky aliphatic amino acid = Ile, Leu,
      Val or Met
<220> FEATURE:
<221> NAME/KEY: MOD_RES
<222> LOCATION: (37)
<223> OTHER INFORMATION: Xaa = any amino acid
<220> FEATURE:
<221> NAME/KEY: MOD_RES
<222> LOCATION: (39)..(41)
<223> OTHER INFORMATION: Xaa = any amino acid
<220> FEATURE:
<221> NAME/KEY: MOD_RES
<222> LOCATION: (43)
<223> OTHER INFORMATION: Xaa = bulky aliphatic amino acid = Ile, Leu,
      Val or Met
<220> FEATURE:
<221> NAME/KEY: MOD_RES
<222> LOCATION: (44)
<223> OTHER INFORMATION: Xaa = any amino acid
<220> FEATURE:
<221> NAME/KEY: MOD_RES
<222> LOCATION: (45)
<223> OTHER INFORMATION: Xaa = bulky aliphatic amino acid = Ile, Leu,
      Val or Met
<220> FEATURE:
<221> NAME/KEY: MOD_RES
<222> LOCATION: (46)..(47)
<223> OTHER INFORMATION: Xaa = any amino acid
<220> FEATURE:
<221> NAME/KEY: MOD_RES
<222> LOCATION: (50)
<223> OTHER INFORMATION: Xaa = any amino acid
<220> FEATURE:
<221> NAME/KEY: MOD_RES
<222> LOCATION: (54)
<223> OTHER INFORMATION: Xaa = any amino acid
<220> FEATURE:
<221> NAME/KEY: MOD_RES
<222> LOCATION: (55)
<223> OTHER INFORMATION: Xaa = bulky aliphatic amino acid = Ile, Leu,
      Val or Met
<220> FEATURE:
<221> NAME/KEY: MOD_RES
<222> LOCATION: (56)
<223> OTHER INFORMATION: Xaa = any amino acid
<220> FEATURE:
<221> NAME/KEY: MOD_RES
<222> LOCATION: (64)
<223> OTHER INFORMATION: Xaa = bulky hydrophobic amino acid = Ile, Leu,
      Val, Met, Phe, Tyr or Trp
<220> FEATURE:
<221> NAME/KEY: MOD_RES
<222> LOCATION: (65)..(69)
<223> OTHER INFORMATION: Xaa = any amino acid
<220> FEATURE:
<221> NAME/KEY: MOD_RES
<222> LOCATION: (71)
<223> OTHER INFORMATION: Xaa = any amino acid
<220> FEATURE:
<221> NAME/KEY: MOD_RES
<222> LOCATION: (72)
<223> OTHER INFORMATION: Xaa = bulky aliphatic amino acid = Ile, Leu,
      Val or Met
<220> FEATURE:
<221> NAME/KEY: MOD_RES
<222> LOCATION: (73)
<223> OTHER INFORMATION: Xaa = any amino acid
<220> FEATURE:
<221> NAME/KEY: MOD_RES
<222> LOCATION: (79)..(80)
<223> OTHER INFORMATION: Xaa = any amino acid
<220> FEATURE:
<221> NAME/KEY: MOD_RES
<222> LOCATION: (81)..(82)
<223> OTHER INFORMATION: Xaa = bulky aliphatic amino acid = Ile, Leu,
      Val or Met
<220> FEATURE:
<221> NAME/KEY: MOD_RES
<222> LOCATION: (86)
```

```
<223> OTHER INFORMATION: Xaa = bulky hydrophobic amino acid = Ile, Leu,
      Val, Met, Phe, Tyr or Trp
<220> FEATURE:
<221> NAME/KEY: MOD_RES
<222> LOCATION: (88)
<223> OTHER INFORMATION: Xaa = any amino acid
<220> FEATURE:
<221> NAME/KEY: MOD_RES
<222> LOCATION: (92)..(93)
<223> OTHER INFORMATION: Xaa = any amino acid
<220> FEATURE:
<221> NAME/KEY: MOD_RES
<222> LOCATION: (95)
<223> OTHER INFORMATION: Xaa = any amino acid
<220> FEATURE:
<221> NAME/KEY: MOD_RES
<222> LOCATION: (97)
<223> OTHER INFORMATION: Xaa = bulky hydrophobic amino acid = Ile, Leu,
      Val, Met, Phe, Tyr or Trp
<220> FEATURE:
<221> NAME/KEY: MOD_RES
<222> LOCATION: (106)..(107)
<223> OTHER INFORMATION: Xaa = any amino acid
<220> FEATURE:
<221> NAME/KEY: MOD_RES
<222> LOCATION: (109)..(110)
<223> OTHER INFORMATION: Xaa = any amino acid
<220> FEATURE:
<221> NAME/KEY: MOD_RES
<222> LOCATION: (117)..(118)
<223> OTHER INFORMATION: Xaa = any amino acid
<220> FEATURE:
<221> NAME/KEY: MOD_RES
<222> LOCATION: (120)..(121)
<223> OTHER INFORMATION: Xaa = any amino acid
<220> FEATURE:
<221> NAME/KEY: MOD_RES
<222> LOCATION: (123)
<223> OTHER INFORMATION: Xaa = any amino acid
<220> FEATURE:
<221> NAME/KEY: MOD_RES
<222> LOCATION: (126)
<223> OTHER INFORMATION: Xaa = bulky aliphatic amino acid = Ile, Leu,
      Val     or Met
<220> FEATURE:
<221> NAME/KEY: MOD_RES
<222> LOCATION: (127)
<223> OTHER INFORMATION: Xaa = any amino acid
<220> FEATURE:
<221> NAME/KEY: MOD_RES
<222> LOCATION: (130)
<223> OTHER INFORMATION: Xaa = any amino acid
<220> FEATURE:
<221> NAME/KEY: MOD_RES
<222> LOCATION: (133)
<223> OTHER INFORMATION: Xaa = acidic amino acid = Arg or Lys
<220> FEATURE:
<221> NAME/KEY: MOD_RES
<222> LOCATION: (134)
<223> OTHER INFORMATION: Xaa = any amino acid
<220> FEATURE:
<221> NAME/KEY: MOD_RES
<222> LOCATION: (138)
<223> OTHER INFORMATION: Xaa = any amino acid
<220> FEATURE:
<221> NAME/KEY: MOD_RES
<222> LOCATION: (140)
<223> OTHER INFORMATION: Xaa = any amino acid
<220> FEATURE:
<221> NAME/KEY: MOD_RES
<222> LOCATION: (143)
<223> OTHER INFORMATION: Xaa = bulky hydrophobic amino acid = Ile, Leu,
      Val, Met, Phe, Tyr or Trp
<220> FEATURE:
<221> NAME/KEY: MOD_RES
<222> LOCATION: (144)
<223> OTHER INFORMATION: Xaa = bulky aliphatic amino acid = Ile, Leu,
      Val or Met
<220> FEATURE:
```

```
<221> NAME/KEY: MOD_RES
<222> LOCATION: (145)
<223> OTHER INFORMATION: Xaa = any amino acid
<220> FEATURE:
<221> NAME/KEY: MOD_RES
<222> LOCATION: (147)..(148)
<223> OTHER INFORMATION: Xaa = any amino acid
<220> FEATURE:
<221> NAME/KEY: MOD_RES
<222> LOCATION: (149)
<223> OTHER INFORMATION: Xaa = bulky aliphatic amino acid = Ile, Leu,
      Val or Met
<220> FEATURE:
<221> NAME/KEY: MOD_RES
<222> LOCATION: (150)..(152)
<223> OTHER INFORMATION: Xaa = any amino acid
<220> FEATURE:
<221> NAME/KEY: MOD_RES
<222> LOCATION: (154)
<223> OTHER INFORMATION: Xaa = bulky aliphatic amino acid = Ile, Leu,
      Val or Met
<220> FEATURE:
<221> NAME/KEY: MOD_RES
<222> LOCATION: (157)
<223> OTHER INFORMATION: Xaa = any amino acid
<220> FEATURE:
<221> NAME/KEY: MOD_RES
<222> LOCATION: (161)
<223> OTHER INFORMATION: Xaa = bulky hydrophobic amino acid = Ile, Leu,
      Val, Met, Phe, Tyr or Trp
<220> FEATURE:
<221> NAME/KEY: MOD_RES
<222> LOCATION: (164)
<223> OTHER INFORMATION: Xaa = any amino acid
<220> FEATURE:
<221> NAME/KEY: MOD_RES
<222> LOCATION: (165)
<223> OTHER INFORMATION: Xaa = bulky aliphatic amino acid = Ile, Leu,
      Val or Met
<220> FEATURE:
<221> NAME/KEY: MOD_RES
<222> LOCATION: (168)
<223> OTHER INFORMATION: Xaa = any amino acid
<220> FEATURE:
<221> NAME/KEY: MOD_RES
<222> LOCATION: (170)
<223> OTHER INFORMATION: Xaa = bulky hydrophobic amino acid = Ile, Leu,
      Val, Met, Phe, Tyr or Trp
<220> FEATURE:
<221> NAME/KEY: MOD_RES
<222> LOCATION: (172)
<223> OTHER INFORMATION: Xaa = any amino acid
<220> FEATURE:
<221> NAME/KEY: MOD_RES
<222> LOCATION: (174)
<223> OTHER INFORMATION: Xaa = any amino acid
<220> FEATURE:
<221> NAME/KEY: MOD_RES
<222> LOCATION: (175)
<223> OTHER INFORMATION: Xaa = bulky aliphatic amino acid = Ile, Leu,
      Val or Met
<220> FEATURE:
<221> NAME/KEY: MOD_RES
<222> LOCATION: (178)
<223> OTHER INFORMATION: Xaa = any amino acid
<220> FEATURE:
<221> NAME/KEY: MOD_RES
<222> LOCATION: (180)..(181)
<223> OTHER INFORMATION: Xaa = any amino acid
<220> FEATURE:
<221> NAME/KEY: MOD_RES
<222> LOCATION: (183)..(184)
<223> OTHER INFORMATION: Xaa = any amino acid
<220> FEATURE:
<221> NAME/KEY: MOD_RES
<222> LOCATION: (186)..(188)
<223> OTHER INFORMATION: Xaa = any amino acid
<220> FEATURE:
<221> NAME/KEY: MOD_RES
```

```
<222> LOCATION: (191)
<223> OTHER INFORMATION: Xaa = any amino acid
<220> FEATURE:
<221> NAME/KEY: MOD_RES
<222> LOCATION: (196)..(197)
<223> OTHER INFORMATION: Xaa = any amino acid
<220> FEATURE:
<221> NAME/KEY: MOD_RES
<222> LOCATION: (200)..(204)
<223> OTHER INFORMATION: Xaa = any amino acid
<220> FEATURE:
<221> NAME/KEY: MOD_RES
<222> LOCATION: (205)..(206)
<223> OTHER INFORMATION: Xaa = bulky aliphatic amino acid = Ile, Leu,
      Val or Met
<220> FEATURE:
<221> NAME/KEY: MOD_RES
<222> LOCATION: (210)..(211)
<223> OTHER INFORMATION: Xaa = any amino acid
<220> FEATURE:
<221> NAME/KEY: MOD_RES
<222> LOCATION: (214)
<223> OTHER INFORMATION: Xaa = any amino acid

<400> SEQUENCE: 1

Xaa Xaa Xaa Xaa Xaa Xaa Cys Val Lys Xaa Ala Xaa Gly Xaa Pro Xaa
  1               5                  10                  15

Xaa Leu Gly Asp Cys Pro Phe Ser Gln Arg Xaa Leu Leu Thr Leu Glu
             20                  25                  30

Glu Lys Lys Xaa Xaa Tyr Xaa Xaa Xaa Leu Xaa Xaa Xaa Xaa Xaa Lys
         35                  40                  45

Pro Xaa Trp Phe Leu Xaa Xaa Xaa Pro Glu Gly Lys Val Pro Val Xaa
     50                  55                  60

Xaa Xaa Xaa Xaa Xaa Lys Xaa Xaa Xaa Asp Ser Asp Val Ile Xaa Xaa
 65                  70                  75                  80

Xaa Xaa Glu Glu Lys Xaa Pro Xaa Pro Ser Leu Xaa Xaa Pro Xaa Glu
                 85                  90                  95

Xaa Ala Ser Val Gly Ser Lys Ile Phe Xaa Xaa Phe Xaa Xaa Phe Leu
            100                 105                 110

Lys Ser Lys Asp Xaa Xaa Asp Xaa Xaa Glu Xaa Ala Leu Xaa Xaa Glu
        115                 120                 125

Leu Xaa Ala Leu Xaa Xaa His Leu Lys Xaa His Xaa Gly Pro Xaa Xaa
    130                 135                 140

Xaa Gly Xaa Xaa Xaa Xaa Xaa Xaa Asp Xaa Ser Leu Xaa Pro Lys Leu
145                 150                 155                 160

Xaa His Leu Xaa Xaa Ala Leu Xaa His Xaa Lys Xaa Trp Xaa Xaa Pro
                165                 170                 175

Glu Xaa Leu Xaa Xaa Val Xaa Xaa Tyr Xaa Xaa Xaa Leu Phe Xaa Arg
            180                 185                 190

Glu Ser Phe Xaa Xaa Thr Lys Xaa Xaa Xaa Xaa Xaa Xaa Xaa Ala Gly
        195                 200                 205

Trp Xaa Xaa Lys Val Xaa
        210

<210> SEQ ID NO 2
<211> LENGTH: 956
<212> TYPE: DNA
<213> ORGANISM: Triticum aestivum
<220> FEATURE:
<223> OTHER INFORMATION: wheat DHAR

<400> SEQUENCE: 2
gcacgagcgc cctctccgct ttcctgctgc tggtgctgtt aaccggactc cccgacgccg     60
```

-continued

```
ccgtcgccgc caacatgacc gaggtctgcg tcaaggccgc cgtcggccac cccgacacgc    120
tcggcgactg tcccttctcc cagagggtgc tgctcacgtt ggaggagaag aaggtgccct    180
accagatgaa gctcatcgac gtcagcaaca agcccgactg gttcctgaag atcaatccag    240
agggcaaggt gcctgtgtat aacggtggtg atggcaaatg gattgctgat tctgatgtga    300
tcactcaagt cattgaggag aagtacccaa ctccatcact tgtgacccct gctgaatatg    360
catcagtggg atcaaagatc ttctccacct tgtcacgtt cttgaagagc aaggatgcca    420
gcgatggttc ggagaaggca cttgttgatg agctgcaggc gctcgaagag cacctgaagg    480
cccatggacc ctacatcaat ggggcgaaca tctccgctgt cgatctcagc ctggctccga    540
agctctacca tctccaggtc gccctggagc acttcaaggg ctggaaggtc cctgaaaccc    600
tgaccagcgt ccatgcctac accgaggctc tcttcagccg cgagtcgttc gtcaagacca    660
aggcgaccaa ggagaacctg atcgccgggt gggcgccgaa agtgaacccg taagccctcc    720
cgccgctcgg agacccggcc cacccccgtc gtgtgagagt agcgacgggc ctcatctgtc    780
taggttggaa taatgcgagc gagccttgat gtgctctggt tgtcgcaaga cgtgcacttg    840
ctgcctgggc tgtgccctgc ctggcttgtg tgtgtgggtg tgggtgatat gtgtgtggtc    900
tgtcctcttt cgtgtgaatg aataatggag ctgcgtaaaa aaaaaaaaaa aaaaaa      956
```

<210> SEQ ID NO 3
<211> LENGTH: 212
<212> TYPE: PRT
<213> ORGANISM: Triticum aestivum
<220> FEATURE:
<223> OTHER INFORMATION: wheat DHAR

<400> SEQUENCE: 3

```
Met Thr Glu Val Cys Val Lys Ala Ala Val Gly His Pro Asp Thr Leu
 1               5                  10                  15

Gly Asp Cys Pro Phe Ser Gln Arg Val Leu Thr Leu Glu Glu Lys
            20                  25                  30

Lys Val Pro Tyr Gln Met Lys Leu Ile Asp Val Ser Asn Lys Pro Asp
        35                  40                  45

Trp Phe Leu Lys Ile Asn Pro Glu Gly Lys Val Pro Val Tyr Asn Gly
    50                  55                  60

Gly Asp Gly Lys Trp Ile Ala Asp Ser Asp Val Ile Thr Gln Val Ile
65                  70                  75                  80

Glu Glu Lys Tyr Pro Thr Pro Ser Leu Val Thr Pro Ala Glu Tyr Ala
                85                  90                  95

Ser Val Gly Ser Lys Ile Phe Ser Thr Phe Val Thr Phe Leu Lys Ser
            100                 105                 110

Lys Asp Ala Ser Asp Gly Ser Glu Lys Ala Leu Val Asp Glu Leu Gln
        115                 120                 125

Ala Leu Glu Glu His Leu Lys Ala His Gly Pro Tyr Ile Asn Gly Ala
    130                 135                 140

Asn Ile Ser Ala Val Asp Leu Ser Leu Ala Pro Lys Leu Tyr His Leu
145                 150                 155                 160

Gln Val Ala Leu Glu His Phe Lys Gly Trp Lys Val Pro Glu Thr Leu
                165                 170                 175

Thr Ser Val His Ala Tyr Thr Glu Ala Leu Phe Ser Arg Glu Ser Phe
            180                 185                 190

Val Lys Thr Lys Ala Thr Lys Glu Asn Leu Ile Ala Gly Trp Ala Pro
```

-continued

```
            195                 200                 205
Lys Val Asn Pro
    210

<210> SEQ ID NO 4
<211> LENGTH: 982
<212> TYPE: DNA
<213> ORGANISM: Zea mays
<220> FEATURE:
<223> OTHER INFORMATION: maize DHAR

<400> SEQUENCE: 4
gcacgagggg ctcgtccgcc cgttgcctgt cgtcgctatg gccgccgtgg aggtgtgcgt     60
gaaggccgcc gcggggaacc ccgacacgct cggcgattgc ccgttctcgc agagggtgct    120
gctcacgctg gaggagaaga aggtcccgta cgaggtgaag ctcgtcgacc tcggcaacaa    180
gcccgaatgg tttctgaaca tcagcccaga gggtaaggtg cctgtgttca cggtggaga     240
tggcaaatgc attgctgatt ctgatgtaat cacccaagtc attgaggaga agttcccgac    300
tccttctctg gtcacccctc agaatatgc atcagtggga tcaaagattt tcccagcctt    360
tgtcaagttc ttgaagagca aggatggtag tgatgggtca gagaaggcgc ttctggatga    420
gctgcaggca ctggatgatc atctcaaagc tcatggcccc tacataaatg gggagaacgt    480
gtcagcgact gatcttagcc tggggccaaa gcttttccac ctacagatcg cactggagca    540
tttcaaaggc tggaagatcc cagaaaacct aaccaatgtc catgcctaca ccaaggctct    600
tttcagccgt gaatcttttg tcaagactaa gccatccgag gagcacgtga ttgcgggatg    660
ggcgcccaag gtgaatgcat aagagccttg tgctttggtg ctacctggtg gactccatcc    720
atttatctta tcagtctttg tcagtggtgt ggataggtgt caagtctgta gcctagatgc    780
atgattcagt tggaattatg cagtgccgtg tctcgagtac tcagttctgg ctgttgcggt    840
tgtgcatctt accttctgtt gctggttttg tttgaggcca tgggcatctc ttggtcctat    900
gctgtgagag cgctgtaatg tgggtaccaa ataatggagc tgcttttatg cttgtggtgt    960
gaaaaaaaaa aaaaaaaaaa aa                                              982

<210> SEQ ID NO 5
<211> LENGTH: 214
<212> TYPE: PRT
<213> ORGANISM: Zea mays
<220> FEATURE:
<223> OTHER INFORMATION: maize DHAR

<400> SEQUENCE: 5

Met Ala Ala Val Glu Val Cys Val Lys Ala Ala Gly Asn Pro Asp
  1               5                  10                  15

Thr Leu Gly Asp Cys Pro Phe Ser Gln Arg Val Leu Leu Thr Leu Glu
                 20                  25                  30

Glu Lys Lys Val Pro Tyr Glu Val Lys Leu Val Asp Leu Gly Asn Lys
             35                  40                  45

Pro Glu Trp Phe Leu Asn Ile Ser Pro Glu Gly Lys Val Pro Val Phe
         50                  55                  60

Asn Gly Gly Asp Gly Lys Cys Ile Ala Asp Ser Asp Val Ile Thr Gln
 65                  70                  75                  80

Val Ile Glu Glu Lys Phe Pro Thr Pro Ser Leu Val Thr Pro Pro Glu
                 85                  90                  95

Tyr Ala Ser Val Gly Ser Lys Ile Phe Pro Ala Phe Val Lys Phe Leu
                100                 105                 110
```

Lys Ser Lys Asp Gly Ser Asp Gly Ser Glu Lys Ala Leu Leu Asp Glu
            115                 120                 125

Leu Gln Ala Leu Asp Asp His Leu Lys Ala His Gly Pro Tyr Ile Asn
        130                 135                 140

Gly Glu Asn Val Ser Ala Thr Asp Leu Ser Leu Gly Pro Lys Leu Phe
145                 150                 155                 160

His Leu Gln Ile Ala Leu Glu His Phe Lys Gly Trp Lys Ile Pro Glu
                165                 170                 175

Asn Leu Thr Asn Val His Ala Tyr Thr Lys Ala Leu Phe Ser Arg Glu
            180                 185                 190

Ser Phe Val Lys Thr Lys Pro Ser Glu Glu His Val Ile Ala Gly Trp
        195                 200                 205

Ala Pro Lys Val Asn Ala
        210

<210> SEQ ID NO 6
<211> LENGTH: 912
<212> TYPE: DNA
<213> ORGANISM: Nicotiana tabacum
<220> FEATURE:
<223> OTHER INFORMATION: tobacco DHAR

<400> SEQUENCE: 6
cgttgctgtc ggttccaaaa gaaagacact atattcaccc agagtagaat tctctagtcc     60
ttaccacact acaaagcgaa aaagctgtag atcaatggct gttgaaatct gtgtcaaggc    120
tgctgtgggt gccctaatg tcctcggaga ctgtccattt agccaaaggg cacttctgac    180
attggaggaa agaaagtgc cttacaagat gcacttgatc aatgttagtg acaagcccaa    240
atggttcttg gaagtgaacc cagaaggaaa agttccagtg atcaagtttg atgaaaaatg    300
gatccctgat tctgatgtta ttgttgggct tcttgaagag aaatacccaa atccctctct    360
ctctagtccc cctgaatttg cttctgtggg ctcgaaaata tttccttcct ttgtctcatt    420
tcggaagagc aaggatgcta gtgacggtac tgagcaggct ctgctcgacg agttaaaggc    480
tttggaagag catctcaagg ctcacggacc atatgtcaat ggggcgaata tttgttcagt    540
cgatttgagt ttggctccga aactgtacca tcttgaggtg gctcttggcc atttcaagaa    600
gtggagtgta cctgaaagct tgagtcatgt gcgtaaatac atgaagttgc tcttcgagcg    660
agagtctttc cagaaaacca aggctgcaaa agagtatgtc attgcaggat gggctccaaa    720
ggtcaatcca tgaaccgatt cataattata atcccgttgt ttcgcaggaa gttagcagtt    780
gaggatacag cattttgaaa tatgaatgta tctcgtaaga tctaaaaatt gttaaatgtt    840
ggatcatgct tgtactgctc tttatgttct aataataag tcatgttcta aaaaaaaaa    900 aaaaaaaaaa aa                                                        912

<210> SEQ ID NO 7
<211> LENGTH: 212
<212> TYPE: PRT
<213> ORGANISM: Nicotiana tabacum
<220> FEATURE:
<223> OTHER INFORMATION: tobacco DHAR

<400> SEQUENCE: 7

Met Ala Val Glu Ile Cys Val Lys Ala Ala Val Gly Ala Pro Asn Val
  1               5                  10                  15

Leu Gly Asp Cys Pro Phe Ser Gln Arg Ala Leu Leu Thr Leu Glu Glu
            20                  25                  30

-continued

```
            Lys Lys Val Pro Tyr Lys Met His Leu Ile Asn Val Ser Asp Lys Pro
                 35                  40                  45

Lys Trp Phe Leu Glu Val Asn Pro Glu Gly Lys Val Pro Val Ile Lys
             50                  55                  60

Phe Asp Glu Lys Trp Ile Pro Asp Ser Asp Val Ile Val Gly Leu Leu
             65                  70                  75                  80

Glu Glu Lys Tyr Pro Asn Pro Ser Leu Ser Thr Pro Glu Phe Ala
                             85                  90                  95

Ser Val Gly Ser Lys Ile Phe Pro Ser Phe Val Ser Phe Leu Lys Ser
                        100                 105                 110

Lys Asp Ala Ser Asp Gly Thr Glu Gln Ala Leu Leu Asp Glu Leu Lys
                        115                 120                 125

Ala Leu Glu Glu His Leu Lys Ala His Gly Pro Tyr Val Asn Gly Ala
                    130                 135                 140

Asn Ile Cys Ser Val Asp Leu Ser Leu Ala Pro Lys Leu Tyr His Leu
            145                 150                 155                 160

Glu Val Ala Leu Gly His Phe Lys Lys Trp Ser Val Pro Glu Ser Leu
                                165                 170                 175

Ser His Val Arg Lys Tyr Met Lys Leu Leu Phe Glu Arg Glu Ser Phe
                            180                 185                 190

Gln Lys Thr Lys Ala Ala Lys Glu Tyr Val Ile Ala Gly Trp Ala Pro
                        195                 200                 205

Lys Val Asn Pro
                210

<210> SEQ ID NO 8
<211> LENGTH: 809
<212> TYPE: DNA
<213> ORGANISM: Arabidopsis thaliana
<220> FEATURE:
<223> OTHER INFORMATION: Arabidopsis DHAR

<400> SEQUENCE: 8
aaagatcgat ggctctagat atctgcgtga aggttgccgt cggtgctcct gatgttctcg      60
gcgactgtcc gtttagccaa cgtgttcttc tgacacttga ggagaagaag cttccctaca     120
agacccatct gattaacgtc tccgacaaac cccaatggtt cttagacatt agtccagagg     180
ggaaagttcc ggtggtgaag cttgatggca atgggtggc tgattctgac gtaattgttg      240
gacttcttga agagaaatat ccagagcctt ctctcaagac tcctcctgaa tttgcttctg     300
taggatccaa atctttggt gcttttgtga cttctcttgaa gagcaaagac gctaatgacg     360
gatccgagaa ggctttggtt gatgagttag aagcgttgga gaatcacttg aagacacatt     420
ctggtccttt tgtagctgga gagaagatta ctgcagtgga tttgagttta gcaccaaagc     480
tttaccatct tgaggttgct cttggtcatt acaagaactg gtctgtccct gagagcttga     540
ccagtgttcg taactacgcc aaggctttgt tctctaggga gtcgtttgag aacaccaagg     600
ctaagaaaga gattgtggtt gcgggttggg aatcgaaggt gaatgcgtga tgtggatcca     660
tgcttctcta gttaatgttg ctttagaact attcttcact gaataataag aatgcacgag     720
tatgtgtgtg ttcttgtttt tgttagagtt ggttatcaat aatgatgcga taaagcagca     780
tagctttttt tgataaaaaa aaaaaaaaa                                       809

<210> SEQ ID NO 9
<211> LENGTH: 213
<212> TYPE: PRT
```

<213> ORGANISM: Arabidopsis thaliana
<220> FEATURE:
<223> OTHER INFORMATION: Arabidopsis DHAR

<400> SEQUENCE: 9

```
Met Ala Leu Asp Ile Cys Val Lys Val Ala Val Gly Ala Pro Asp Val
1               5                   10                  15

Leu Gly Asp Cys Pro Phe Ser Gln Arg Val Leu Thr Leu Glu Glu
            20                  25                  30

Lys Lys Leu Pro Tyr Lys Thr His Leu Ile Asn Val Ser Asp Lys Pro
        35                  40                  45

Gln Trp Phe Leu Asp Ile Ser Pro Glu Gly Lys Val Pro Val Val Lys
    50                  55                  60

Leu Asp Gly Lys Trp Val Ala Asp Ser Asp Val Ile Val Gly Leu Leu
65                  70                  75                  80

Glu Glu Lys Tyr Pro Glu Pro Ser Leu Lys Thr Pro Glu Phe Ala
                85                  90                  95

Ser Val Gly Ser Lys Ile Phe Gly Ala Phe Val Thr Phe Leu Lys Ser
            100                 105                 110

Lys Asp Ala Asn Asp Gly Ser Glu Lys Ala Leu Val Asp Glu Leu Glu
        115                 120                 125

Ala Leu Glu Asn His Leu Lys Thr His Ser Gly Pro Phe Val Ala Gly
    130                 135                 140

Glu Lys Ile Thr Ala Val Asp Leu Ser Leu Ala Pro Lys Leu Tyr His
145                 150                 155                 160

Leu Glu Val Ala Leu Gly His Tyr Lys Asn Trp Ser Val Pro Glu Ser
                165                 170                 175

Leu Thr Ser Val Arg Asn Tyr Ala Lys Ala Leu Phe Ser Arg Glu Ser
            180                 185                 190

Phe Glu Asn Thr Lys Ala Lys Lys Glu Ile Val Val Ala Gly Trp Glu
        195                 200                 205

Ser Lys Val Asn Ala
    210
```

<210> SEQ ID NO 10
<211> LENGTH: 711
<212> TYPE: DNA
<213> ORGANISM: Lycopersicon esculentum
<220> FEATURE:
<223> OTHER INFORMATION: tomato DHAR

<400> SEQUENCE: 10

```
cagaattctc tctgttcatc aatcatggtt gttgaagttt gtgtcaaggc tgctgtgggt      60
gcccctgatg tccttggaga ctgtccattt agccaaaggg tacttctgac attggaggaa     120
aagaaagtga cttacaagaa gcacttgatc aatgttagtg acaagcccaa atggttcttg     180
gaggtgaacc ctgaagggaa agttcccgtg atcaattttg gtgacaaatg atcccagat     240
tctgatgtca ttgttgggat tattgaagag aaataccca atccctctct cattgctccc     300
cctgaatttg cctctgtggg ctcgaaaata tttcctacct tcgtctcatt tctgaagagc     360
aaggattcta gtgacagtac tgagcaggct ctccttgatg aactaaaggc tttggaagag     420
catctcaagg ctcatggacc atatatcaat gggcagaatg tttgttcagt tgatatgagc     480
ttggctccaa aactgtacca tctcgaggtg gctcttggac acttcaagaa gtggagtgtg     540
cctgaaagct tgagtcatgt gcgtaactac atgaagctgc tcttcgagcg agagtcgttc     600
cagaaaacca aggctgaaga gaagtacgtc atcgcagggt gggctccaaa agtttaacgt     660
```

```
atgactgact ccaaactata atcatgtttt gtctcgagta gttagcaatt c          711
```

<210> SEQ ID NO 11
<211> LENGTH: 210
<212> TYPE: PRT
<213> ORGANISM: Lycopersicon esculentum
<220> FEATURE:
<223> OTHER INFORMATION: tomato DHAR

<400> SEQUENCE: 11

```
Met Val Glu Val Cys Val Lys Ala Ala Val Gly Ala Pro Asp Val
 1               5                  10                  15

Leu Gly Asp Cys Pro Phe Ser Gln Arg Val Leu Thr Leu Glu Glu
                20                  25                  30

Lys Lys Val Thr Tyr Lys Lys His Leu Ile Asn Val Ser Asp Lys Pro
                35                  40                  45

Lys Trp Phe Leu Glu Val Asn Pro Glu Gly Lys Val Pro Val Ile Asn
        50                  55                  60

Phe Gly Asp Lys Trp Ile Pro Asp Ser Asp Val Ile Val Gly Ile Ile
65                  70                  75                  80

Glu Glu Lys Tyr Pro Asn Pro Ser Leu Ile Ala Pro Pro Glu Phe Ala
                85                  90                  95

Ser Val Gly Ser Lys Ile Phe Pro Thr Phe Val Ser Phe Leu Lys Ser
                100                 105                 110

Lys Asp Ser Ser Asp Ser Thr Glu Gln Ala Leu Leu Asp Glu Leu Lys
                115                 120                 125

Ala Leu Glu Glu His Leu Lys Ala His Gly Pro Tyr Ile Asn Gly Gln
        130                 135                 140

Asn Val Cys Ser Val Asp Met Ser Leu Ala Pro Lys Leu Tyr His Leu
145                 150                 155                 160

Glu Val Ala Leu Gly His Phe Lys Lys Trp Ser Val Pro Glu Ser Leu
                165                 170                 175

Ser His Val Arg Asn Tyr Met Lys Leu Leu Phe Glu Arg Glu Ser Phe
                180                 185                 190

Gln Lys Thr Lys Ala Glu Glu Lys Tyr Val Ile Ala Gly Trp Ala Pro
        195                 200                 205

Lys Val
    210
```

<210> SEQ ID NO 12
<211> LENGTH: 1044
<212> TYPE: DNA
<213> ORGANISM: Oryza sativa
<220> FEATURE:
<223> OTHER INFORMATION: rice DHAR

<400> SEQUENCE: 12

```
aaaatcttct cttcccgtac gtgagaagcg ccaggtcgtc gtcgccgcca tgggcgtgga   60
ggtgtgcgtc aaggccgccg tcggccaccc ggacacgctc ggcgactgtc cattctcgca  120
gagggtgctg ctgactctgg aggagaagaa ggtgccctac gagatgaagc tcatcgacgt  180
ccagaacaac cccgactggt ttctgaagat cagcccagag gggaaggtgc ctgtgtttaa  240
cggtggtgat ggcaaatgga ttcctgattc tgatgtgatc actcaagtca ttgaggaaa  300 gtacccaacc ccgtctcttg tcaccccctcc tgagtatgca tcagtgggat caaaaatttt  360
ctcatgcttc acaacgttct tgaagagcaa ggatccaaat gatggttcag agaaggcact  420
```

-continued

```
tcttactgaa ctgcaggcac tcgaggagca tctgaaagct catggcccct ttatcaacgg      480
gcagaacatt tcagctgctg accttagcct ggcaccaaag ctctaccatc tccaggttgc      540
tctggagcat ttcaaaggct ggaagatccc ggaagaccta accaatgttc atgcttacac      600
agaggctctg tttagccgcg aatctttcat caagacgaag gcagctaagg agcacctgat      660
tgctggatgg gcaccaaaag tgaatgcgta agagcctgcc cttatgctct ggtgctgctt      720
ggacaccatg ctgtttatct gatcggtcca tgtcagtggt gggcactact actactcttg      780
tgtagcttgg gtgcatgatt gggttggaat aatgtagcct catccgttga gtaccttgat      840
atggttgttg caagtgtgca cttttctat gaactatctc ctgctggctt aagtcgaaac       900
cgtgggtcgg tttggcctta tgttcaacta agagagtgca tatactgtaa tggaaccttt      960
gctagtacaa tatgttatat gaataatgga gatgcagcct gcagctgctc ttgcttggag      1020
cttaaaaaaa aaaaaaaaaa aaaa                                             1044
```

<210> SEQ ID NO 13
<211> LENGTH: 213
<212> TYPE: PRT
<213> ORGANISM: Oryza sativa
<220> FEATURE:
<223> OTHER INFORMATION: rice DHAR

<400> SEQUENCE: 13

```
Met Gly Val Glu Val Cys Val Lys Ala Ala Val Gly His Pro Asp Thr
 1               5                  10                  15

Leu Gly Asp Cys Pro Phe Ser Gln Arg Val Leu Leu Thr Leu Glu Glu
            20                  25                  30

Lys Lys Val Pro Tyr Glu Met Lys Leu Ile Asp Val Gln Asn Lys Pro
        35                  40                  45

Asp Trp Phe Leu Lys Ile Ser Pro Glu Gly Lys Val Pro Val Phe Asn
    50                  55                  60

Gly Gly Asp Gly Lys Trp Ile Pro Asp Ser Asp Val Ile Thr Gln Val
65                  70                  75                  80

Ile Glu Glu Lys Tyr Pro Thr Pro Ser Leu Val Thr Pro Pro Glu Tyr
                85                  90                  95

Ala Ser Val Gly Ser Lys Ile Phe Ser Cys Phe Thr Thr Phe Leu Lys
            100                 105                 110

Ser Lys Asp Pro Asn Asp Gly Ser Glu Lys Ala Leu Leu Thr Glu Leu
        115                 120                 125

Gln Ala Leu Glu Glu His Leu Lys Ala His Gly Pro Phe Ile Asn Gly
    130                 135                 140

Gln Asn Ile Ser Ala Ala Asp Leu Ser Leu Ala Pro Lys Leu Tyr His
145                 150                 155                 160

Leu Gln Val Ala Leu Glu His Phe Lys Gly Trp Lys Ile Pro Glu Asp
                165                 170                 175

Leu Thr Asn Val His Ala Tyr Thr Glu Ala Leu Phe Ser Arg Glu Ser
            180                 185                 190

Phe Ile Lys Thr Lys Ala Ala Lys Glu His Leu Ile Ala Gly Trp Ala
        195                 200                 205

Pro Lys Val Asn Ala
    210
```

<210> SEQ ID NO 14
<211> LENGTH: 1063
<212> TYPE: DNA
<213> ORGANISM: Spinacia oleracea
<220> FEATURE:
<223> OTHER INFORMATION: spinach DHAR
<220> FEATURE:
<221> NAME/KEY: modified_base
<222> LOCATION: (1036)
<223> OTHER INFORMATION: n = g, a, c or t

<400> SEQUENCE: 14

```
gcgaaatgtc gaccgttaaa ataacaccag tcgcgtattc actttcatca tcgaccctca      60
aacgccagct aatcccaaat ccccaattcc accgccgcaa tcgcaccatt ttcacccagc     120
atttcaagaa cggaacccaa agaaacctta ctgtgtccat gtctagttcg acccactcc     180
aaatatgcgt caaggaatct gtcaccaccc ccaacaagct tggcgattgt ccattttgcc     240
aaagagtgtt gttgacttta gaagaaaagc atctccctta tgatatgaag ctggtagact     300
taagtaacaa gccagagtgg tttacaaata tcaatccaga tggtaaagta cctgtggtga     360
aattcgatga aaattgggtt gcagattcag atatcatcgc aaagtcccta gaagagagat     420
acccaaatcc acctttggca cacctgacga agaagagttc agttggctca aaaatctttc     480
ctgcatttgt tggttttatt aaaagcaagg accccagcga tggaaaagag cagggattac     540
tgaacgagct cagttccttc aatgattacc tgaaagaaaa tggacctttt atcaacgggg     600
agaagatctc tgctgcggac ctagctcttg gaccaaagct ttaccatatg gagattgcat     660
tgggacatta caagaattgg tcagttccag agtcacttcc gtatgtgaag tcttatatga     720
agaatatatt ttccagggat tcatttgtga aaacaattgc atcaacgaga gatgtgattg     780
ccggctgggc aaagcacaca agctgaagct gtccaagata tatgggcact ttgattccct     840
gcaggaagac tacccttggt gtgaatggtt gggtcttaag atatcaaaat gattttggca     900
acttgcaatg gcttgaatgt aaattaagca tcctaattgt gtagtgttgt aaagacttgt     960
atacttacaa aatccatgaa aagtgttcag tgtgaaaata ttaaatgtcg ggtaatccat    1020
ggtcacatta acatcnaaaa aaaaaaaaaa aaaaaaaaa aaa                       1063
```

<210> SEQ ID NO 15
<211> LENGTH: 266
<212> TYPE: PRT
<213> ORGANISM: Spinacia oleracea
<220> FEATURE:
<223> OTHER INFORMATION: spinach DHAR

<400> SEQUENCE: 15

```
Met Ser Thr Val Lys Ile Thr Pro Val Ala Tyr Ser Leu Ser Ser
 1               5                  10                  15

Thr Leu Lys Arg Gln Leu Ile Pro Asn Pro Gln Phe His Arg Arg Asn
                20                  25                  30

Arg Thr Ile Phe Thr Gln His Phe Lys Asn Gly Thr Gln Arg Asn Leu
            35                  40                  45

Thr Val Ser Met Ser Ser Ser Asp Pro Leu Gln Ile Cys Val Lys Glu
        50                  55                  60

Ser Val Thr Thr Pro Asn Lys Leu Gly Asp Cys Pro Phe Cys Gln Arg
    65                  70                  75                  80

Val Leu Leu Thr Leu Glu Glu Lys His Leu Pro Tyr Asp Met Lys Leu
                85                  90                  95

Val Asp Leu Ser Asn Lys Pro Glu Trp Phe Thr Asn Ile Asn Pro Asp
                100                 105                 110

Gly Lys Val Pro Val Val Lys Phe Asp Glu Asn Trp Val Ala Asp Ser
            115                 120                 125
```

```
-continued

Asp Ile Ile Ala Lys Ser Leu Glu Glu Arg Tyr Pro Asn Pro Pro Leu
    130             135                 140

Ala Thr Pro Asp Glu Lys Ser Ser Val Gly Ser Lys Ile Phe Pro Ala
145             150                 155                 160

Phe Val Gly Phe Ile Lys Ser Lys Asp Pro Ser Asp Gly Lys Glu Gln
                165                 170                 175

Gly Leu Leu Asn Glu Leu Ser Ser Phe Asn Asp Tyr Leu Lys Glu Asn
            180                 185                 190

Gly Pro Phe Ile Asn Gly Glu Lys Ile Ser Ala Ala Asp Leu Ala Leu
        195                 200                 205

Gly Pro Lys Leu Tyr His Met Glu Ile Ala Leu Gly His Tyr Lys Asn
    210             215                 220

Trp Ser Val Pro Glu Ser Leu Pro Tyr Val Lys Ser Tyr Met Lys Asn
225             230                 235                 240

Ile Phe Ser Arg Asp Ser Phe Val Lys Thr Ile Ala Ser Thr Glu Asp
                245                 250                 255

Val Ile Ala Gly Trp Ala Lys His Thr Ser
            260             265
```